(12) United States Patent
Tagg et al.

(10) Patent No.: US 9,107,780 B2
(45) Date of Patent: Aug. 18, 2015

(54) DISPOSABLE PAD FOR CHILDREN'S OUTFIT

(71) Applicants: Stephen David Tagg, Red Deer (CA); Michelle Lynn Tagg, Red Deer (CA)

(72) Inventors: Stephen David Tagg, Red Deer (CA); Michelle Lynn Tagg, Red Deer (CA)

(73) Assignee: 1567958 Alberta Ltd., Red Deer (CA)

( * ) Notice: Subject to any disclaimer, the term of this patent is extended or adjusted under 35 U.S.C. 154(b) by 0 days.

(21) Appl. No.: 13/789,395

(22) Filed: Mar. 7, 2013

(65) Prior Publication Data
US 2014/0257225 A1  Sep. 11, 2014

(51) Int. Cl.
*A61F 13/15* (2006.01)
*A61F 13/56* (2006.01)

(52) U.S. Cl.
CPC .......... *A61F 13/5611* (2013.01); *A61F 13/15* (2013.01); *A61F 2013/15048* (2013.01); *A61F 2013/15146* (2013.01)

(58) Field of Classification Search
CPC .......... A61F 13/5611; A61F 13/15; A61F 2013/15048; A61F 2013/15146
USPC .......... 604/385.01, 349, 385.13, 385.05, 604/385.03
See application file for complete search history.

(56) References Cited

U.S. PATENT DOCUMENTS

| | | | |
|---|---|---|---|
| 3,871,027 | A | 3/1975 | Orr |
| 4,330,888 | A | 5/1982 | Klepfer |
| 6,114,597 | A | 9/2000 | Romare |
| 6,168,583 | B1 | 1/2001 | Tanji et al. |
| 6,212,683 | B1 | 4/2001 | Liebmann |
| 6,450,998 | B1 | 9/2002 | Otsubo et al. |
| 6,753,455 | B2 | 6/2004 | Chmielewski |
| 2006/0106356 | A1* | 5/2006 | McVicker et al. ........ 604/385.01 |
| 2007/0197984 | A1* | 8/2007 | Richardson et al. .......... 604/348 |
| 2008/0039813 | A1 | 2/2008 | Ford et al. |
| 2009/0110862 | A1 | 4/2009 | Karg |
| 2011/0301559 | A1* | 12/2011 | Sasayama et al. ............ 604/364 |

FOREIGN PATENT DOCUMENTS

| | | |
|---|---|---|
| CA | 2041278 | 10/1992 |
| CA | 2316900 | 1/1999 |

\* cited by examiner

*Primary Examiner* — Jacqueline Stephens
(74) *Attorney, Agent, or Firm* — Richard D. Okimaw

(57) ABSTRACT

A disposable protection pad is proposed for adhering to infant's clothing for guarding the clothing from soiling due to waste leakage from a diaper worn by the infant. The protection pad has a fluid-pervious front sheet, a fluid-impervious back sheet, and a fluid-absorbent core between the front and the back sheets. An adhesive means is provided on the rear surface of the back sheet, such that the protection pad can be releasably adhered to the inner surface of the clothing. The protection pad is oval shaped having a broader middle region and with narrower top and bottom edges. The protection pad is preferably provided with pull tabs and leg notches.

6 Claims, 4 Drawing Sheets

DISPOSABLE PAD FOR CHILDREN'S OUTFIT

BACKGROUND OF THE INVENTION

1. Field of Invention

The present disclosure relates to the protection of clothing from human body discharges.

2. Description of Related Art

Diapers are generally disposable and are worn by infants or the sick/aged to absorb and retain their waste fluid. Such diapers are in use for collecting the body-waste and thereby for protecting the clothing worn from getting soiled. Depending on the severity of the discharges, the frequency of change for the disposable diapers is generally determined. The designs, materials and the sizes of the diapers may also be determined based on the usage and the user, the purpose being to absorb, spread out and retain the waste.

A difficulty presently exists when the wearer is lying down. In such situations, the waste may be prone to flowing or being forced in a direction up the user's back thereby bypassing the diaper and coming into contact with the wearer's clothing. In particular, diapers are commonly closely fitted to the body, hence in order to comply with the body shape need to be narrowed at the bottom and between the thighs though the collection of waste is maximum at the bottom. Although the materials of the diapers are meant to absorb, spread out and retain the waste within the diaper area, often the waste overflows out particularly from the narrowed bottom and the backside above the hip region. Such a leakage requires replacement of the clothing in addition to the replacement of the diaper. Previous devices have not provided an adequate a way to protect this region of clothing from such contact.

Canadian Patent Application No. 2,041,278 discloses a disposable pad for protecting clothing from perspiration. The pad is constructed of disposable paper and plastic pressed in layers and backed with an adhesive. The pad is embossed such that the size can be adjusted by tearing off sections of the pad. After use the pad is disposed by pulling the adhesive backed pad from the clothing.

U.S. Pat. No. 3,871,027 discloses a disposable absorptive pad for protecting the clothing of the user while burping a baby or alternatively, to use as a bib.

The pad comprises a layer of relatively impervious material overlain by a co-extensive layer of an absorbent material and is contoured to encircle a child's neck when attached by adhesive means as a bib. Alternatively, it may be adapted to fit a person's shoulder by the adhesive means for protecting the clothing of the user.

U.S. Pat. No. 4,330,888 discloses a disposable bib, napkin or apron of a flexible sheet material having a neck cutout in its upper edge portion and two shoulder pieces adjacent the cut out. The upper edge portion carries a pressure sensitive adhesive capable of releasably adhering to the clothing or to the body of the user.

US Patent Application Publication No. 2008/0039813 discloses a diaper pad of an absorptive layer adapted to absorb and retain waste expelled by an infant that is not captured by the disposable diaper. The pad has a water resistant layer behind the absorptive layer. The water resistant layer is provided with an adhesive layer for securing the pad to the clothing worn by the infant. The diaper pad forms an extension of the backside of the diaper above the hip region.

SUMMARY OF THE INVENTION

According to a first embodiment of the present invention there is disclosed a disposable protection pad for adhering to infant's clothing for guarding the clothing from soiling due to waste leakage from a diaper worn by the infant. The protection pad has a fluid-pervious front sheet, a fluid-impervious back sheet, and a fluid-absorbent core between the front and the back sheets. An adhesive means is provided on the rear surface of the back sheet, such that the protection pad can be releasably adhered to the inner surface of the clothing. The protection pad is oval shaped having a broader middle region and with narrower top and bottom edges. The pad may also include pull tabs and leg notches.

Since the proposed protection pad is adhered to the inner surface of the clothing, it is more comfortable for the infant than to guard leakage by having to wear a bigger sized diaper or having tighter elastics at the leg or hip openings of the diaper.

This proposed approach is also beneficial over having a diaper pad like in US Patent Application Publication No. 2008/0039813, where the diaper pad is an extension of the diaper and needs to be adhered to the inner surface of the clothing, thereby causing discomfort to the infant due to being attached to the clothing. This discomfort is likely to increase when the clothing is heavier, such as winter clothing. Unlike with the diaper pad, advantageously, in the proposed approach, positioning the protection pad on the inner surface of the clothing for adhering can be more conveniently done before the diaper worn infant is made to wear the clothing.

Advantageously again, in this approach, the oversized protection pad can be positioned on the inner surface of the clothing with its broader middle region to cover both the bottom and the backside hip region of the diaper where most overflow is expected.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention wherein similar characters of reference denote corresponding parts in each view.

DETAILED DESCRIPTION

Figure 1:
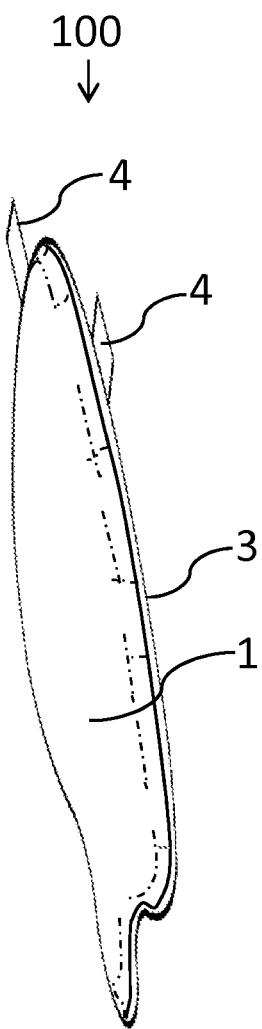
FIG. 1 is a perspective view of the disposable protection pad, according to an embodiment of the disclosure.
Figure 2:
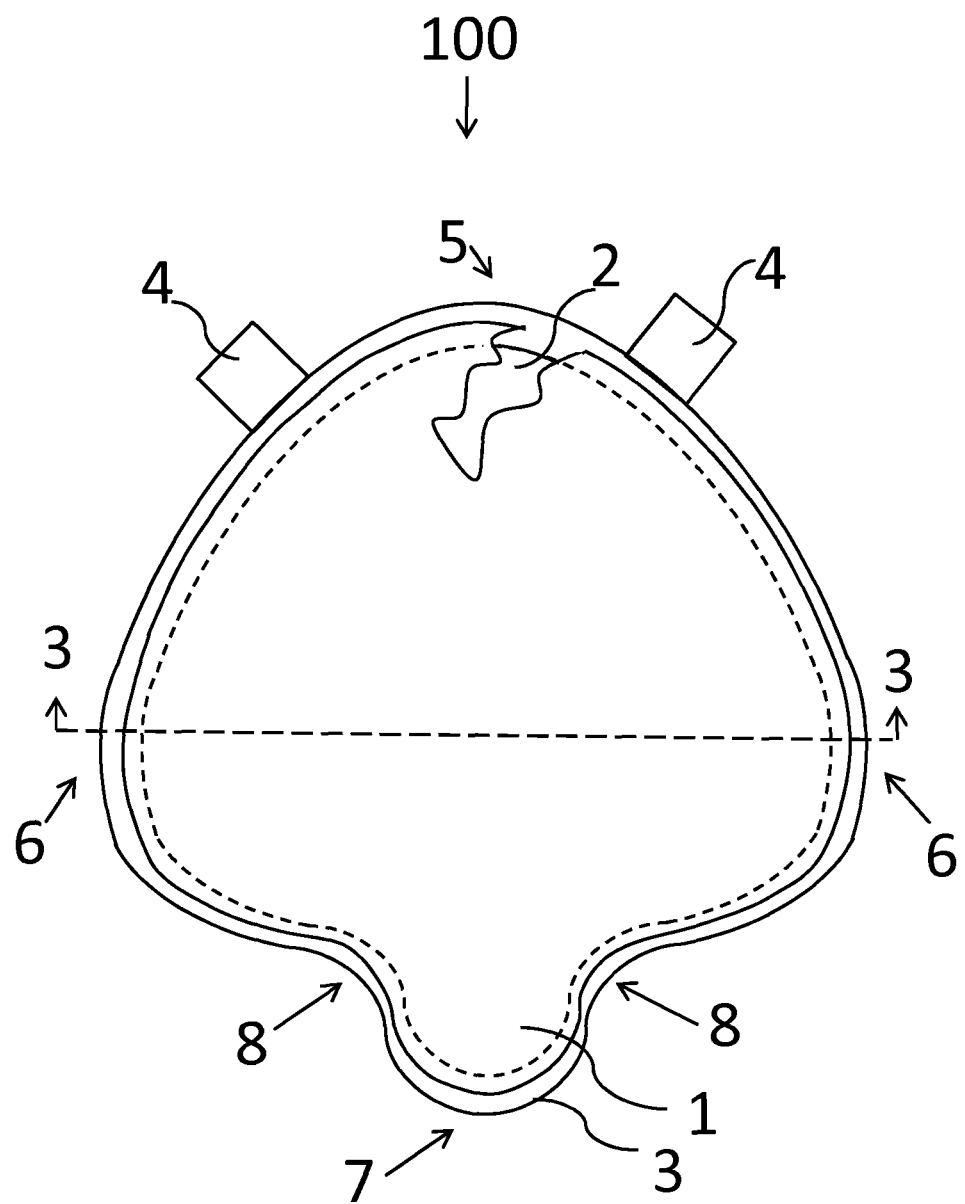
FIG. 2 is a plan view of the front side of the protection pad of FIG. 1.

Referring to FIGS. 1 and 2, a disposable protection pad for adhering to clothing for guarding the clothing from getting soiled due to waste leakage from the diaper according to a first embodiment of the invention is shown generally at 100. The disposable protection pad 100 is suitable for adhering to an infant's clothing for guarding the clothing from soiling due to waste leakage from a diaper worn by the infant.

Figure 3:
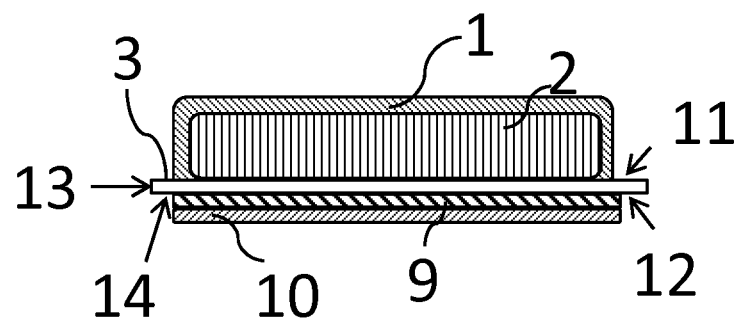
FIG. 3 is a cross-sectional view of the protection pad along the cut-line 3-3 shown in FIG. 2.

The protection pad 100 is formed with a substantially fluid-impervious back sheet 3, a substantially fluid-pervious front sheet 1 and a substantially fluid-absorbent core 2 disposed therebetween. The protection pad 100 has a substantially oval outline with a broader middle region and narrower top and bottom edge and includes an adhesive layer 9 disposed the rear thereof as will be more fully described below. The back sheet 3 has front 11 and rear 12 surfaces and a substantially oval-shaped outline with a broader middle region 6 and narrower top 5 and bottom 7 edges. As illustrated in FIG. 3, the front surface 11 of the back sheet 3 faces the absorbent core 2. The front sheet 1 is substantially fluid-pervious, having an outline corresponding substantially to the back sheet 3. The substantially fluid-absorbent core 2 is disposed between the front sheet 1 and the back sheet 3. The adhesive layer 9 is disposed on at least a portion of the rear surface 12 of the back sheet 3, such that the protection pad 100 can be releasably adhered to the inner surface of the clothing by applying mild pressure on the protection pad 100.

The front sheet 1 is preferably compliant, soft feeling and non-irritating to the infant's skin. Further, it is fluid pervious for permitting fluids like faeces or urine to readily penetrate through its thickness, so as to give a dry feel to the infant. It may be made up of any suitable material available in the art, such as, by way of non-limiting example, bound, non-woven fibre cloth, so-called non-woven materials, perforated plastic films, nets as well as open-cell or perforated foam materials. The top sheet 1 may be a mono- or a multi-layered structure.

The absorbent core 2 may again be a single- or a multi-layered structure that is capable of absorbing, storing and distributing the fluid. Any type of material that suits this purpose, such as, by way of non-limiting example, natural fibers like wood or cotton fibers, synthetic fibers like polymeric fibers, super absorbent polymers or from a combination of natural and synthetic fibers may be used.

The purpose of the back sheet 3 is to prevent the fluid absorbed and contained in the absorbent core 2 from wetting the clothing that contacts the protection pad 100. The back sheet 3 is substantially impervious to the waste fluids and is preferably manufactured from a thin plastic film. The back sheet 3 has is substantially flexible is such that it readily conforms to the general shape and contours of the clothing to which it is to be applied. The back sheet 3 typically extends across the whole of the absorbent core 2 and can further extend to form wholly or partially side wrappings or wings.

The protection pad 100 extends beyond the diaper leakage areas when worn and provides protection to the clothing where the leakage. As illustrated in FIG. 3, towards the protection pad 100 includes an outer peripheral edge having along which the front sheet 1 and the back sheet 3 are joined up together so as to encase the absorbent core 2 completely. This is preferred such that the fluid absorbed in the absorbent core 2 is retained and not leaked out from the edges of the absorbent core 2.

Figure 4:
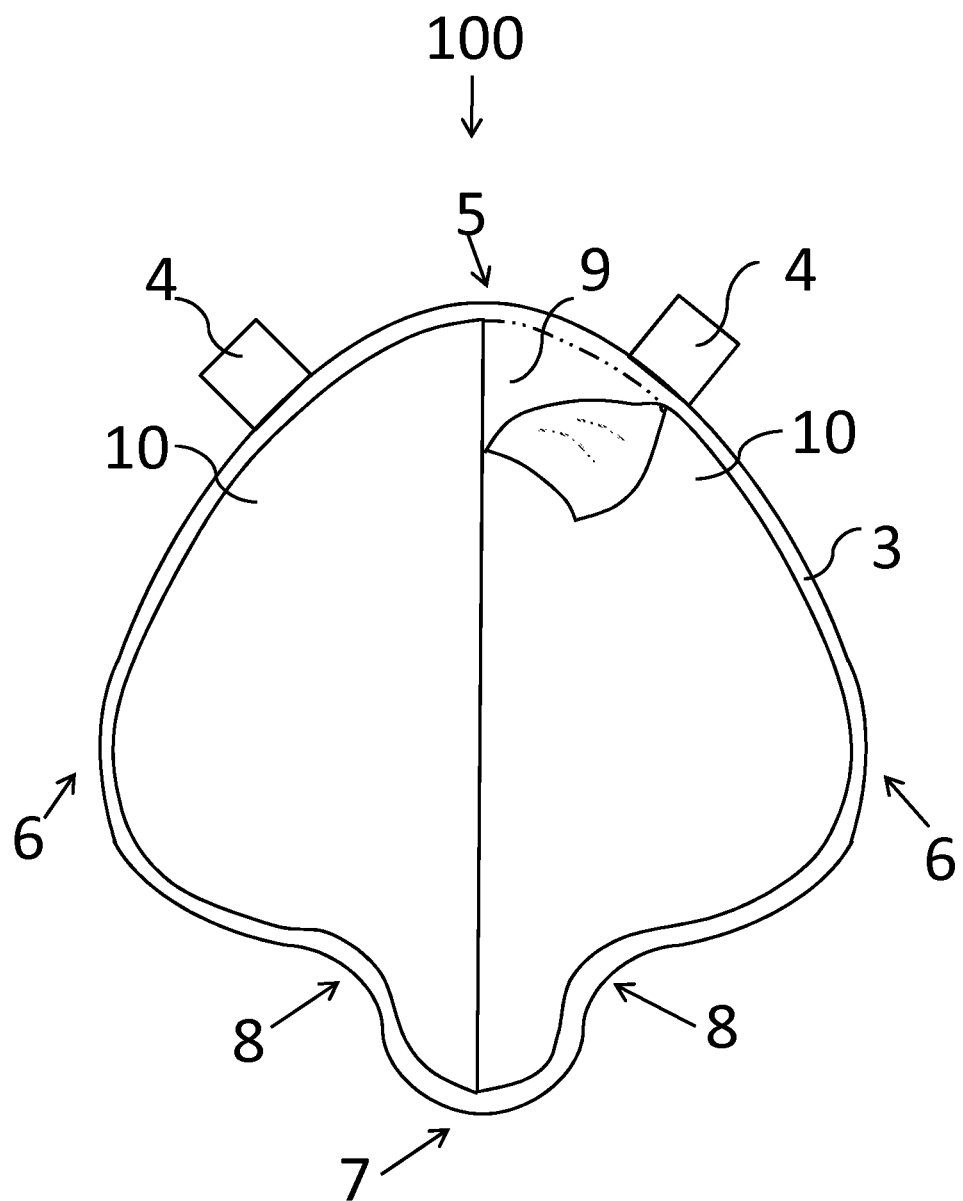
FIG. 4 is a plan view of the back side of the protection pad.

As illustrated in the FIGS. 1, 2 and 4, the peripheral edge 13 of the protection pad 100 is oval shaped with a broader middle region 6 and narrower top 5 and bottom edges 7. The size of the protection pad 100 may be suitably determined, depending on the age of the infant to be used for. As for example, for a new born to up to about three years old infant, a typical size for the middle region 6 may range from about 4 inches to 10 inches (102 to 254 mm) and the length between the top 5 and the bottom 7 edges may also range from about 5 inches to 14 inches (127 to 356 mm). However, it will be appreciated that other sizes may also be useful as well.

As illustrated in FIGS. 1, 2 and 4, pull tabs 4 may optionally be provided proximate to the top edge 5 of the protection pad 100 for pulling out the adhered protection pad 100 from the clothing, after use. According to other embodiments, the pull tabs 4 may be positioned at other positions, such as one at the top edge 5 and one at the bottom edge 7, if that makes the process of pulling out easier. The pull tabs 4 may be an extension of the back sheet 3 or may be formed of a different suitable material if that is more effective in pulling out the protection pad 100 and may be adhered or otherwise connected to the one or more of the back sheet 3, front sheet 1 or absorbent core 2. As illustrated, two pull tabs 4 may be utilized, although it will be appreciated that other quantities may be used as well.

The leg notches 8 are provided towards the bottom edge 7. The leg notches 8 are useful particularly if the protection pad 100 is meant for adhering inside trouser like clothing or diapers. As shown in FIGS. 2a and 3, the shape of the leg notches 8 may be designed like inward curvature such that the protection pad 100 is easier to conform to the shape inside the trouser like clothing. Variations to this shape may also be possible. The size of the leg notches and the extent of the curvature may be suitably determined, particularly depending on the size of the protection pad 100 and the kind of the trousers meant to be used with. By way of non-limiting example, the leg notches 8 may have be formed with a substantially arcuate shape having a radius of between ½ and 2 inches (12 and 51 mm), although it will be appreciated that other shapes and dimensions may be utilized as well.

The adhesive means 9 provided on the rear surface 12 of the back sheet 3 may be any type as available in the art. The purpose of the adhesive means 9 is to adhere the protection pad 100 to the internal surface of the clothing by applying a light pressure on the protection pad 100. The adhesive means 9 may be such as a chemical adherent or a fiber-engaging physical adherent. The adhesive means 9 may be preferably provided on substantially the whole of the rear surface 12 of the back sheet 3, for a better adherence. However, this is not a must. According to other embodiments, the adhesive means 9 may be provided only at selected locations on the rear surface 12 of the back sheet 3 such as, by way of non-limiting example, leaving a strip, generally indicated at 14, of the back sheet 3 proximate to the peripheral edge 13 which free of any adhesive. It will be appreciated that in such embodiments, such adhesiveless strip 14 may permit a user to grasp such peripheral edge to remove the pad from clothing. Such clear strip may have any width as desired by a user, such as, by way of non-limiting example, up to 1 inch (25 mm). The protection pad 100 may optionally include a peeling layer 10 covering the adhesive layer so as to prevent adhesion to unwanted surfaces. By way of non-limiting example, the peeling layer 10 may comprise a sheet of plastic, wax paper or the like. In FIG. 3, the protection pad 100 is shown to have a peeling layer 10 in two halves instead of being in a single piece, as smaller areas are generally more convenient to peel off. In one half, the peeling layer 10 is shown to be partially peeled off, with the other half being yet to be peeled before exposing the full area of the adhesive means 9 for adhering the protection pad 100 to the clothing. According to other embodiments, the peeling layer 10 may be in a single piece or in more than two pieces, if that makes the process of peeling easier to expose the chemical adherent. For the fiber-engaging physical adherent, generally no peeling layer 10 needs to be used. However, this is not a limitation and a suitable kind of a peeling layer 10 may be used as well.

As to further discussion of the manner of usage and operation of the present invention, the same should be apparent from the above description.

Accordingly, no further discussion relating to the manner of usage and operation will be provided.

While specific embodiments of the invention have been described and illustrated, such embodiments should be considered illustrative of the invention only and not as limiting the invention as construed in accordance with the accompanying claims.

What is claimed is:

1. An apparatus for adhering to infant's clothing for guarding the clothing from soiling due to waste leakage from a diaper worn by the infant, the apparatus comprising:

a substantially fluid-impervious back sheet, said back sheet having front and rear surfaces and a substantially oval-shaped outline with a broader middle region and narrower top and bottom edges;

a substantially fluid-pervious front sheet having an outline corresponding substantially to said back sheet, a substantially fluid-absorbent core disposed between said front sheet and said front surface;

an adhesive layer disposed on at least a portion of said rear surface, such that the apparatus is releasably adherable to the inner surface of the clothing; and leg notches disposed towards said bottom edge so as to form an extension therebetween wherein said extension tapers to a narrowed distal end.

2. The apparatus of claim 1 further comprising at least one pull tab that is disposed towards said top edge of the apparatus, for pulling out the adhered apparatus from the clothing after use.

3. The apparatus of claim 1 wherein said adhesive means is selected from the group consisting of chemical adherents and fiber-engaging physical adherents.

4. The apparatus of claim 3 wherein said chemical adherent type adhesive means is protected with a plurality of peeling layers for removal before adhering the apparatus to the clothing.

5. The apparatus of claim 1 wherein said middle region extends over a length ranging between about four to about ten inches.

6. An apparatus for adhering to infant's clothing for guarding the clothing from soiling due to waste leakage from a diaper worn by the infant, the apparatus comprising:

a substantially fluid-impervious back sheet, said back sheet having front and rear surfaces and a substantially oval-shaped outline with a broader middle region and narrower top and bottom edges;

a substantially fluid-pervious front sheet having an outline corresponding substantially to said back sheet, a substantially fluid-absorbent core disposed between said front sheet and said front surface;

an adhesive layer disposed on at least a portion of said rear surface, such that the apparatus is releasably adherable to the inner surface of the clothing;

a first and a second pull tabs being disposed towards said top edge for pulling out the adhered apparatus from the clothing after use; and leg notches disposed towards said bottom edge so as to form an extension therebetween wherein said extension tapers to a narrowed distal end.

* * * * *